United States Patent [19]

Dieterich

[11] 4,143,062

[45] Mar. 6, 1979

[54] STABILIZED PREPARATIONS OF AROMATIC ISOCYANATO SULPHONIC ACIDS

[75] Inventor: Dieter Dieterich, Leverkusen, Fed. Rep. of Germany

[73] Assignee: Bayer Aktiengesellschaft, Leverkusen, Fed. Rep. of Germany

[21] Appl. No.: 825,881

[22] Filed: Aug. 19, 1977

[30] Foreign Application Priority Data

Sep. 7, 1976 [DE] Fed. Rep. of Germany ....... 2640103

[51] Int. Cl.² .......................................... C07C 119/048
[52] U.S. Cl. ........................ 260/453 SP; 260/453 AR
[58] Field of Search ................... 260/453 AR, 453 SP

[56] References Cited

U.S. PATENT DOCUMENTS

| 3,826,769 | 7/1974 | Carlson ...................... 260/29.2 TN |
| 3,959,329 | 5/1976 | Dieterich et al. ............ 260/453 AR |

*Primary Examiner*—Dolph H. Torrence
*Attorney, Agent, or Firm*—Gene Harsh; Lawrence S. Pope

[57] ABSTRACT

The present invention is concerned with a method of imparting storage stability to aromatic isocyanato sulphonic acids and to the stabilized mixtures so prepared. The aromatic isocyanates are combined with liquids which are non-polar, inert non-solvents having boiling points above 90° C. either before or after they are sulphonated to prepare the acids. The stabilized mixtures contain between about 80 to 10 wt. % of the inert liquids and about 20 to 80 wt. % of the acids.

3 Claims, No Drawings it has not been established in industrial use.

STABILIZED PREPARATIONS OF AROMATIC ISOCYANATO SULPHONIC ACIDS

BACKGROUND OF THE INVENTION

Sulphonic acids of aromatic diisocyanates or polyisocyanates are known. They may be prepared in a simple manner by reacting the corresponding aromatic diisocyanates or polyisocyanates with sulphonating agents, such as sulphur trioxide, adducts of sulphur trioxide, oleum, chlorosulphonic acid or sulphuric acid (see, for example, German Offenlegungsschrift Nos. 2,227,111 and 2,359,615 and U.S. Pat. No. 3,826,769).

The products obtained may be solid, resinous or pulverulent sulphonation products or solutions of the sulphonated isocyanates in unreacted starting isocyanate, depending on the isocyanate used and the degree of sulphonation.

Whereas the handling of liquid sulphonated polyisocyanates entails no difficulties, considerable problems arise in the preparation, storage and use of solid isocyanato sulphonic acids in powder form.

In many cases, these products are obtained in such a finely divided form that they are difficult to separate and purify from the liquid reaction medium. The dried products raise dust when being put into containers or transferred. The most serious problem, however, is that dry powders prepared in this way are not stable in storage. The melting point and decomposition point rise during storage and the products become progressively more insoluble in organic solvents, as well as in the polyesters, polyethers and polyols normally used for the preparation of polyurethanes.

Although instability in storage is a general problem with polyisocyanates and is therefore well-known to those skilled in the art, in the case of solid pulverulent isocyanato sulphonic acids the deterioration in the quality sets in within such a short time after their preparation, for example, in some cases, after only a few days, that commercial production of usable polyaddition products is thereby rendered very difficult if not impossible.

On the other hand, there is a technological and economic demand for using polyisocyanato sulphonic acids in polyaddition chemistry in addition to or instead of the conventional diisocyanates and polyisocyanates because they are excellent starting materials for the production of hydrophilic polyurethanes, in particular polyurethanes which are water dispersible, and because they are very suitable physiologically and from the point of view of industrial hygiene since they have no vapor pressure and give rise to water-soluble amino sulphonic acids on decomposition. The preparation of polyurethanes from sulphonated tolylene diisocyanate has hitherto been carried out either by sulphonating the diisocyanate prepolymer instead of the pure diisocyanate (U.S. Pat. No. 3,826,769) or by preparing the isocyanato sulphonic acid only shortly before it is converted to the polyurethane (U.S. Pat. No. 3,826,769). The first method has the disadvantage of limiting the choice of sulphonating agents since, for example, sulphur trioxide causes decomposition phenomena when reacted with polyether prepolymers. If sulphuric acid is used as sulphonating agent, the resulting reaction is inevitably accompanied by chain-lengthening with formation of urea groups. Moreover, this method may only be used for sulphonating completely or partly free isocyanates, but not for sulphonating products in the form of urethanes. This means that, in the case of an isocyanate prepolymer, only the isocyanate end groups may be sulphonated. The second method cannot be carried out on a technical scale since the polyurethane manufacturer cannot be expected to carry out a process of isocyanate sulphonation prior to preparing the polyurethane.

It has also been proposed (U.S. Pat. No. 3,826,769) to dissolve the isocyanato sulphonic acids in an organic solvent, such as acetone, immediately after their preparation and to use them as solutions. This method is also impracticable since, for example, a solution of sulphonated tolylene diisocyanate in acetone is stable for at the most a few hours, after which it rapidly becomes cloudy and forms a precipitate.

It is therefore not surprising that solid isocyanato sulphonic acids have not hitherto become established in industrial use.

The problem therefore existed of preparing isocyanato sulphonic acids or stabilizing them in such a manner that they could be stored and used without problems and that solutions thereof in organic media would have a long storage life.

SUMMARY OF THE INVENTION

The present invention provides a solution to this problem. It has surprisingly been found that isocyanato sulphonic acids may be effectively stabilized by the addition of a non-polar, inert, high-boiling liquid which does not dissolve the aromatic isocyanato sulphonic acids at room temperature, in other words it acts as dispersing agent. The addition of only about 10% of such a dispersing agent is sufficient to stabilize the isocyanato sulphonic acids, a slightly moist, non-dusting powder being obtained. If desired, however, substantially larger quantities of dispersing agent may be used and the suspensions of polyisocyanato sulphonic acids or pasty products then obtained are easy to handle.

The present invention thus relates to a process for increasing the stability in storage of finely dispersed, solid aromatic isocyanato sulphonic acids obtained by the sulphonation of aromatic isocyanates, characterized in that:

a. sulphonation of the aromatic isocyanates is carried out in the presence of an inert liquid which is not a solvent for the aromatic sulphonic acids and which has a boiling point above 90° C., at least some of the said liquid remaining in the sulphonation product after termination of the sulphonation; or b. solid, finely dispersed aromatic isocyanato sulphonic acids which have been prepared in the absence of a liquid of the type defined under (a) above are mixed with such a liquid.

The present invention also relates to mixtures in the form of moist powders, pastes or suspensions which are stable in storage, containing:

a. from about 20 to 90%, by weight, of solid, finely dispersed aromatic isocyanato sulphonic acids; and b. from about 80 to 10%, by weight, of a non-polar liquid having a boiling point above 90° C. which is inert towards isocyanate groups and sulphonic acid groups and incapable of dissolving the aromatic isocyanato sulphonic acids mentioned under (a).

DETAILED DESCRIPTION OF THE INVENTION

Virtually any solid aromatic isocyanato sulphonic acids of the type obtained in a finely divided form by sulphonating mono-, di- or poly-isocyanates are suitable as aromatic isocyanato sulphonic acids to be stabilized according to the present invention, for example the sulphonation products of phenylisocyanate, p-tolylisocyanate, p-chlorophenylisocyanate, p-nitrophenylisocyanate, p-methoxyphenylisocyanate, m-chlorophenylisocyanate, m-chloromethylphenylisocyanate, p-chloromethylphenylisocyanate, 4,4'-stilbenediisocyanate, 4,4'-dibenzyldiisocyanate, 3,3'- and 2,2'-dimethyl-4,4'-diisocyanatodiphenylmethane, 2,5,2',5'-tetramethyl-4,4'-diisocyanatodiphenylmethane, 3,3'-dimethoxy-4,4'-diisocyanatodiphenylmethane, 3,3'-dichloro-4,4'-diisocyanato-diphenylmethane, 4,4'-diisocyanato-dimethylmethane, 4,4'-diisocyanatodiphenylcyclohexylmethane, 4,4'-diisocyanato-benzophenone, 4,4'-diisocyanato-diphenylsulphone, 4,4'-diisocyanatodiphenylether, 4,4'-diisocyanato-3,3'-dibromo-diphenylmethane, 4,4'-diisocyanato-3,3'-diethyl-diphenylmethane, 4,4'-diisocyanato-diphenyl-ethylene-(1,2), 4,4'-diisocyanatodiphenyl-sulphide, 1,3- and 1,4-phenylene diisocyanate, 2,4- and 2,6-tolylenediisocyanate and mixtures of these isomers, diphenylmethane-2,4'- and/or -4,4'-diisocyanate, naphthylene-1,5-diisocyanate, triphenylmethane-4,4',4"-triisocyanate, polyphenyl-polymethylene polyisocyanates which are obtainable by aniline-formaldehyde condensation followed by phosgenation and which have been described, for example, in British Pat. Nos. 874,430 and 848,671, polyisocyanates containing carbodiimide groups as described in German Pat. No. 1,092,007, the diisocyanates described in U.S. Pat. No. 3,492,330, polyisocyanates containing allophanate groups as described, for example, in British Pat. No. 994,890, Belgian Pat. No. 761,626 and published Dutch Pat. Application No. 7,102,524, polyisocyanates containing isocyanurate groups as described in German Pat. Nos. 1,022,789; 1,222,067 and 1,027,394 and in German Offenlegungsschrift Nos. 1,929,034 and 2,004,048, polyisocyanates containing acylated urea groups according to German Pat. No. 1,230,778, and polyisocyanates containing biuret groups as described, for example, in German Pat. No. 1,101,394, British Pat. No. 889,050 and French Pat. No. 7,017,514.

Pulverulent sulphonated di- and tri-isocyanates are preferred, particularly the monosulphonic and disulphonic acids of 4,4'-diisocyanatodiphenylmethane, 2,4'-diisocyanatodiphenylmethane and, in particular, 2,4'-diisocyanatotoluene and 2,6-diisocyanatotoluene and mixtures of these isomers, all of which acids are generally obtained in their dimeric form. Methods of preparing these pulverulent polyisocyanates have been described, for example, in U.S. Pat. No. 3,826,769 and in German Pat. application Nos. P 25 24 476.2 and P 26 15 876.9.

Pulverulent, aromatic isocyanato sulphonic acids which are to be stabilized according to the present invention are generally obtained when sulphonation is carried out in excess isocyanate or an inert organic dispersing agent, such as dichloroethane or tetrachloroethane, by methods analogous to those described in the aforesaid literature. The particle size of the isocyanato sulphonic acids obtained as fine powders may be regulated by suitable choice of the dispersing agent, the temperature at which sulphonation is carried out and the speed of stirring during sulphonation. The particle size is generally reduced by the addition of surface active agents. The aromatic isocyanato sulphonic acids to be stabilized according to the present invention generally have an average particle diameter of from about 0.0005 to 0.5 mm.

Partially sulphonated liquid aromatic polyisocyanate mixtures, such as those described, for example, in German Offenlegungsschrift Nos. 2,227,111; 2,359,614 and 2,359,615 and U.S. Pat. No. 3,959,329, herein incorporated by reference are not isocyanato sulphonic acids of the type which are to be stabilized according to the present invention.

The mixtures according to the present invention which are stable in storage contain a second stabilizing component consisting of inert organic liquids which have boiling points above 90° C., preferably above 110° C., and are substantially non-polar and immiscible with water and, moreover, do not act as solvents for the isocyanato sulphonic acids.

Examples of such compounds include, in particular, aliphatic, cycloaliphatic and aromatic hydrocarbons, e.g. heptane, octane, isooctane, nonane, decane, undecane or eicosane, as well as mixtures of these hydrocarbons of the type found in commercial petroleum hydrocarbon and paraffin oil fractions, mineral spirits and mineral oils, for example solvent naphtha, cleaning petrol, petroleum, paraffin oil, polymerized olefins, such as liquid polypropylene and polybutylene, tetraisobutene, methylcyclohexane, cyclododecane, dimethylcyclohexane, turpentine oil and decalin.

Other suitable aromatic hydrocarbons include toluene, o-, m- and p-xylene, commercial aromatic mixtures, cumene, pseudocumene, hemellitol, p-cumene, tetramethylbenzene, diisopropylbenzenes, isododecylbenzene and tetralin. Halogenated hydrocarbons, ketones, esters and ethers could also be used provided they are sufficiently non-polar, i.e. do not dissolve the isocyanato sulphonic acid. This is generally the case if the proportion of pure hydrocarbon in the dispersing agent amounts to at least 70%, by weight. The following are examples: dibutylether, di-sec-butylether, diisoamylether, methylisobutyl ketone, 4-heptanone, 5-methyl-3-heptanone, 2-undecanone, dinonyl ketone, dioctylphthalate, trioctylphthalate and dioctyladipate.

Another group of suitable substances are the perchlorinated hydrocarbons, e.g. highly chlorinated paraffins, as well as chlorobenzene, dichlorobenzene and chlorocyclohexane.

It will be clear from the list given above that "inert liquids" in the context of the present invention are liquids which show no reactivity towards sulphonic acid groups and isocyanate groups. Liquids which fulfill this requirement and conform to the conditions defined above are suitable for method (b) of carrying out the process according to the present invention.

Liquids which are used for method (a) of the process according to the present invention must in addition be inert towards the sulphonating agents under the reaction conditions employed. Most of the exemplified liquids are inert towards sulphonating agents and may therefore also be used as solvents for sulphonation according to method (a). As is well known, aromatic hydrocarbons are normally capable of sulphonation on their own. Their use is not subject to any restrictions if they are added to the reaction mixture after sulphonation in accordance with method (b). Their use as solvents for the isocyanates which are to be sulphonated is, however, possible only if they react considerably more slowly with the sulphonating agents than the isocyanates which are to be sulphonated or if a small amount of sulphonation of these hydrocarbons is acceptable.

Thus, for example, chlorobenzene and dichlorobenzene may be used as solvents for sulphonation, whereas toluene, xylene and cumene are preferably added after sulphonation. In the preparation of isocyanato polysulphonic acids (derivatives containing more than one sulphonic acid group per molecule of starting isocyanate used for sulphonation) it is necessary to take into account that disulphonation proceeds much more slowly and with greater difficulty than monosulphonation. In such cases, therefore, only solvents which are inert towards sulphur trioxide should be used for sulphonation. Moreover, in the case of the above-mentioned polysulphonic acids, stabilization according to the present invention takes place independently of the nature of the stabilizing agent used according to the present invention, preferably only after sulphonation and after removal of excess sulphonating agent in accordance with method (b).

The process according to the present invention for stabilizing isocyanato sulphonic acids may be carried out according to two embodiments:

Sulphonation of the isocyanate may be carried out as described in the above literature references, for example, but the liquid which is essential according to the present invention is added before or during sulphonation to the isocyanate which is to be sulphonated. Part of the additive used may then be removed after termination of the sulphonating reaction, for example by filtration or suction filtration. The only essential condition in this embodiment of the process is that a sufficient quantity of the liquid which is essential according to the present invention should be left in the sulphonation product to correspond to the proportions of the components in the mixtures according to the present invention.

Sulphonation may also be carried out in the absence of the liquids according to the present invention, for example as described in the above literature references, and the product obtained, which may still be moist and contain a residue of auxiliary solvents, such as dichloroethane, or a residue of unsulphonated liquid starting isocyanate, may then be mixed with the dispersing agent according to the present invention. What is essential is that the sulphonated isocyanate should be completely enveloped or penetrated by the dispersing agent according to the present invention as soon after its preparation as possible without, however, being dissolved therein.

The mixtures according to the present invention are moist powders, pastes or suspensions, depending on the quantity of dispersing agent present in the mixtures according to the present invention. The quantity of the dispersing agent which is essential according to the present invention, that is to say in the first embodiment of the process the quantity of dispersing agent left in the mixture, should be such that the resulting mixtures contain from about 20 to 90%, by weight, preferably from about 50 to 85%, by weight, of aromatic isocyanato sulphonic acids and from about 80 to 10%, by weight, preferably from about 15 to 50%, by weight, of the stabilizing liquid which is essential according to the present invention. The average particle diameter of the finely dispersed isocyanato sulphonic acids is from about 0.5 to 500 micron. Exceptionally finely divided and sedimentation-resistant suspensions of sulphonated isocyanates are obtained if the dispersing agent which is essential to the present invention is used as reaction medium for sulphonation. In this case, the starting material is dissolved in the liquid according to the present invention and thereafter sulphonated analogously to the method described in the above literature references, the sulphonated isocyanate being obtained directly as a suspension according to the present invention.

The stabilized preparations according to the present invention may contain additives which increase the stabilizing effect or produce additional stabilizing effects, such as resistance to yellowing. Such additives include light protective agents well known in the art, such as sterically hindered phenols, U.V. absorbents and conventional unsulphonated polyisocyanates, in particular aliphatic polyisocyanates having a low vapor pressure, as well as organopolysiloxanes and chlorofluorinated hydrocarbon oils. The stabilized preparations are stable under conditions of storage and transport and are suitable for the preparation of various polyurethanes, such as elastomers, foams, coatings, molded products and adhesives. Whereas hydrocarbons, such as octane, toluene or xylene, evaporate during or after preparation or application of the polyurethane, high boiling products, such as phosphates, phthalates or polychloroparaffins, are left in the polyurethane end-product as plasticizers or in the form of micro-droplets.

The stabilized isocyanato sulphonic acids are soluble in polyesters and polyethers even after prolonged storage. The polyurethanes produced from them are free from irregularities and cloudiness.

One particular advantage of the pastes and moist powders according to the present invention is their low requirement in liquid components for the preparation of reaction mixtures or their reduced viscosity at a given formulation. Furthermore, the quantity of air inevitably introduced when preparing the mixture is considerably less and the mixtures contain few or no foam bubbles and give rise to more homogeneous reaction mixtures.

EXAMPLES

EXAMPLE 1

1914 g (11 mole) of tolylene diisocyanate (isomeric mixture 2,4:2,6 = 80:20) are reacted with 335 g (4.2 mole) of sulphur trioxide at from 23° to 30° C. for about 20 hours with stirring, a thick liquid suspension of dimeric tolylene diisocyanate monosulphonic acid in tolylene diisocyanate being obtained. Sulphur trioxide is liberated from heated 65% oleum by means of a slow stream of nitrogen and conducted as a gas diluted with nitrogen over the surface of the stirred isocyanate. The resulting suspension is diluted with 500 ml of toluene and suction filtered and the solid residue is suspended twice with 500 ml of toluene and suction filtered. The product, still moist with toluene, is filled into containers. Yield: 1285 g, toluene content 23%, weight of dry substance 990 g, corresponding to 93% of the theoretical yield.

The product is a slightly moist powder which may easily be handled without causing dust. It may easily be poured into containers or from one container to another, does not cake together and does not stick to a spatula.

Comparison experiment 200 g of the moist powder obtained according to Example 1 are dried in a vacuum drying cupboard at 50° C. and the dry powder is filled into containers. Yield: 154 g. The product causes dust during transfer into containers.

EXAMPLE 2

13 g of the product obtained according to Example 1 and stored for one month are dissolved in 100 g of tetrahydrofuran. A clear solution is obtained, which shows very slight cloudiness after one hour.

When the process is repeated using 10 g of the dry powder obtained from the comparison experiment, a cloudy solution is obtained and a precipitate forms after one hour.

EXAMPLE 3

1.3 g of the product obtained according to Example 1 and stored for one month are dissolved in 10 g of acetone. A clear solution is obtained. Severe cloudiness appears after 3 hours due to reaction with acetone. When this process is repeated using 1 g of the dry powder from the comparison experiment, a very cloudy solution is obtained and a floccular precipitate rapidly separates from the solution.

EXAMPLE 4

26 g of the product prepared according to Example 1 and stored for two months are dissolved in 100 g of trischloroethylphosphate at 50° C. A clear, low viscosity solution is obtained. It undergoes no change within 10 days. When this process is repeated using 20 g of the dry powder from the comparison experiment, a very cloudly solution is obtained which becomes viscous after 3 days and gels after 8 days. The same poor result is obtained when 20 g of dry powder which has been stored for two months are made up into a paste using 6 g of toluene and then dissolved.

EXAMPLE 5

13 g of the product obtained according to Example 1 and stored for one month are mixed with 100 g of tetraethyleneglycol at room temperature and stirred. A clear solution is obtained on heating. When this experiment is repeated using 10 g of the dry powder obtained from the comparison experiment, the mixture must be heated to 60° C. to form a solution. The solution is slightly cloudy.

EXAMPLE 6

13 g of the product obtained according to Example 1 and stored for two months are mixed with 100 g of adipic acid/diethylglycol polyester (OH-No. 56, molecular weight 2000) and 20 g of toluene at 50° C. and stirred. A clear, viscous solution is obtained. When the experiment is carried out using 10 g of the dry powder from the comparison experiment, a more highly viscous, very cloudy solution is obtained.

EXAMPLE 7

A solution of 43.5 g (0.25 mole) of tolylene diisocyanate (isomeric mixture 80:20) in 102 g of a chlorinated paraffin ("Witachlor 40 NV", manufacturers: Dynamit Nobel; chlorine content of 40%) is sulphonated using 22 g of sulphur trioxide as in Example 1. A 30% dispersion of sulphonated isocyanate in chloroparaffin is obtained. Sedimentation sets in when the dispersion is left to stand for a prolonged period. The sediment is redispersible even after prolonged storage. The stored samples are readily soluble in tetrahydrofuran, trischloroethylphosphate and polypropyleneglycol (MW 2000). The solutions are clear.

EXAMPLE 8

A solution of 87 g (0.5 mole) of tolylene diisocyanate (isomeric mixture 80:20) in 87 g of anhydrous chlorobenzene is sulphonated with 40 g (0.5 mole) of sulphur trioxide as in Example 1. A remarkably stable, finely divided dispersion of the sulphonated isocyanate in chlorobenzene is obtained. Sedimentation begins to appear only after 3 days. The sediment remains redispersible even after prolonged storage. The stored samples are readily soluble in tetrahydrofuran, tris-chloroethylphosphate and polypropyleneglycol (MW 2000). The solutions are clear. The same results are obtained when 4,4'-diphenylmethane diisocyanate is used instead of tolylenediisocyanate.

EXAMPLE 9

A solution of 261 g (1.5 mole) of tolylene-2,4-diisocyanate in 700 g of 1,2-dichloroethane is sulphonated using 120 g of sulphur trioxide as in Example 1. The resulting suspension is suction filtered and the filter residue is washed with dichloroethane and again vigorously suction filtered. 50 g of the product are mixed with 10 g of dioctylphthalate while still moist to form a paste. After one month, the product forms a clear solution in tetrahydrofuran and polypropyleneglycol.

EXAMPLE 10

50 g of the product obtained in Example 9 are triturated with 10 g of paraffin oil in a mortar to form a paste. A thick paste which is capable of forming a clear solution in tetrahydrofuran after one month is obtained.

EXAMPLE 11

50 g of the product obtained in Example 9 are mixed with 10 g of trioctylphosphate. A dispersion which dissolves to a clear solution in tetrahydrofuran or polypropyleneglycol is still obtained after one month.

EXAMPLE 12

26 g of the product obtained according to Example 1 and stored for two months are mixed at 70° C. with 100 g of a polypropyleneglycol having a molecular weight of 2000 and stirred. A clear solution of the reaction product is obtained. When the experiment is carried out using 20 g of the dry powder from the comparison experiment, a milky solution is obtained.

The same result is obtained using a product which has been stored for four months. This product also dissolves after prolonged stirring at 40° C.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Mixture in the form of a moist powder, paste or suspension which is stable in storage, containing:
   a. from 20 to 90%, by weight, of solid, finely dispersed aromatic isocyanato sulphonic acids which are solids at room temperature; and
   b. from 80 to 10%, by weight, of a non-polar liquid having a boiling point above 90° C. which is inert towards isocyanate groups and sulphonic acid groups and does not dissolve the aromatic isocyanato sulphonic acids mentioned under (a).

2. The storage stable mixtures of claim 1, wherein the aromatic isocyanato sulphonic acids are obtained by the sulphonation of toluene diisocyanate.

3. The mixture of claim 2, wherein an 80:20 isomeric mixture of 2,4- and 2,6-toluene diisocyanate is employed.

* * * * *